United States Patent [19]

Moss

[11] Patent Number: 5,520,662
[45] Date of Patent: May 28, 1996

[54] GASTROINTESTINAL ASPIRATING AND FEEDING DEVICE WITH REMOVABLE SLEEVE

[76] Inventor: Gerald Moss, R.D. #1, West Sand Lake, N.Y. 12196

[21] Appl. No.: 303,428

[22] Filed: Sep. 9, 1994

[51] Int. Cl.$^6$ ..................................................... A61M 5/00
[52] U.S. Cl. ............................................ 604/246; 604/280
[58] Field of Search .................................. 604/270, 246, 604/249, 264, 265, 268, 280, 171, 173–176

[56] References Cited

U.S. PATENT DOCUMENTS

| 954,494 | 4/1910 | Andrews | 604/249 X |
|---|---|---|---|
| 4,270,542 | 6/1981 | Plumley | 604/270 X |
| 4,543,089 | 9/1985 | Moss . | |
| 4,642,092 | 2/1987 | Moss . | |
| 4,643,712 | 2/1987 | Kulik et al. | 604/4 |
| 4,735,605 | 4/1988 | Swartz . | |
| 4,968,306 | 11/1990 | Huss et al. | 604/264 |
| 5,066,278 | 11/1991 | Hirschberg et al. | 604/256 |
| 5,076,787 | 12/1991 | Overmyer . | |
| 5,215,539 | 6/1993 | Schoolman . | |
| 5,320,328 | 6/1994 | Decloux et al. . | |

FOREIGN PATENT DOCUMENTS 1662580  7/1991  U.S.S.R. .................... 604/270

*Primary Examiner*—Corrine M. McDermott
*Attorney, Agent, or Firm*—Schmeiser, Olsen & Watts

[57] ABSTRACT

A gastrointestinal aspirating and feeding device having at least one feeding orifice and a plurality of aspirating orifices. A removable sleeve is utilized to selectively control the number of operational aspirating orifices.

4 Claims, 2 Drawing Sheets

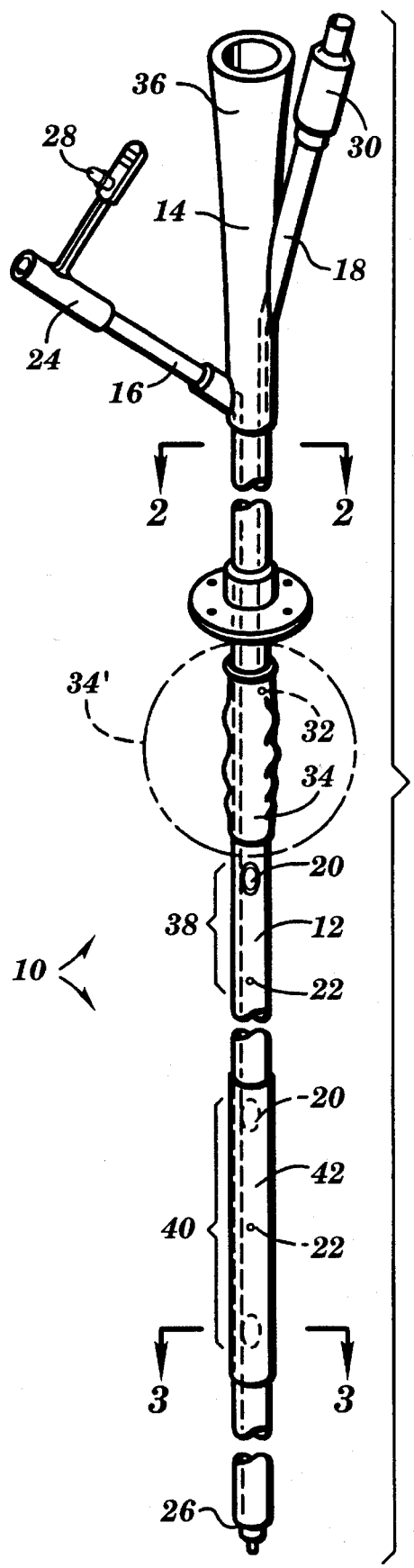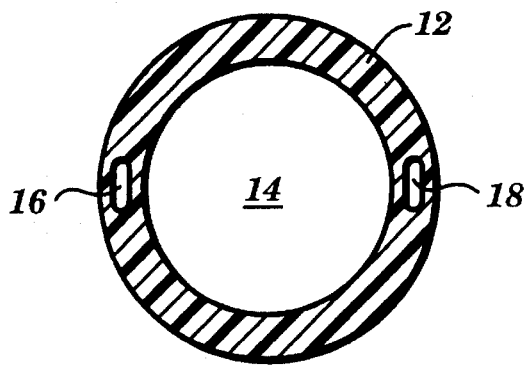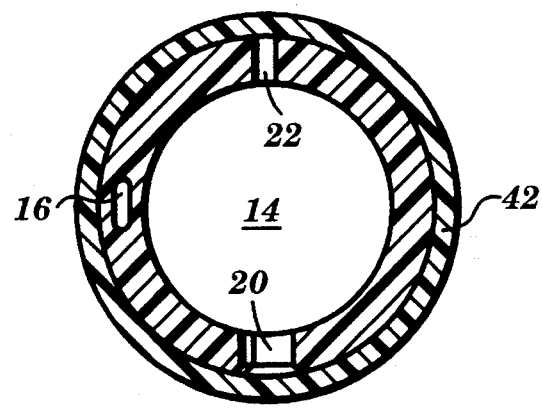

GASTROINTESTINAL ASPIRATING AND FEEDING DEVICE WITH REMOVABLE SLEEVE

FIELD OF THE INVENTION

The present invention relates to a medical device and, more particularly, to a gastrointestinal aspirating and feeding device having a plurality of aspirating orifices. The gastrointestinal aspirating and feeding device includes a removable sleeve for selectively controlling the number of operational aspirating orifices.

BACKGROUND OF THE INVENTION

Post-operatively, gastrointestinal functions usually deteriorate. The causes of this deterioration are varied and include such factors as the use of anesthesia or pain killing drugs, and the manipulation of the bowel during the operation. Additionally, air swallowed by the patient contributes to gastrointestinal malfunctions since the gas is inefficiently propelled through the digestive tract. This causes a problem commonly known as abdominal distention which not only impairs bowel function and interferes with the rate of absorption of nutrients through the bowel, but often prevents the patient from breathing deeply or coughing, which can lead to severe pulmonary difficulties. In severe cases, the pressure caused by the abdominal distention has been known to break open the patient's wound. One of the indirect effects of abdominal distention is the fact that due to the pain associated with it, and the lesser rate of bowel absorption, the patient often becomes undernourished which slows the healing process. It has, therefore, been a long-standing objective of the medical profession to prevent abdominal distention while providing sufficient nutrition in order to speed the patient's recovery.

U.S. Pat. No. 4,543,089 to Moss, incorporated herein by reference, discloses a gastrointestinal aspirating and feeding device which is designed to effectively eliminate abdominal distention while simultaneously providing a patient with sufficient nutrition. The gastrointestinal aspirating and feeding device generally includes a tube having a feeding lumen and an aspirating lumen which are inserted gastrally into a patient. Preferably, the aspirating lumen includes a plurality of aspirating orifices, and the feeding lumen includes an orifice positioned adjacent a distal end of the tube.

Upon proper insertion of the gastrointestinal aspirating and feeding device into the body of a patient, the feeding orifice is disposed in the proximal duodenum. Upstream from the feeding orifice, a first set of aspirating orifices is positioned within the terminal portion of the stomach, the pylorus and/or the proximal duodenum. In addition, further upstream from the first set of aspirating orifices, a second set of aspirating orifices is positioned within the main body of the stomach.

U.S. Pat. No. 4,642,092 to Moss, incorporated herein by reference, again discloses a gastrointestinal aspirating and feeding device which is designed to effectively eliminate abdominal distention while simultaneously providing a patient with sufficient nutrition. As in the '089 patent to Moss, the gastrointestinal aspirating and feeding device includes a tube having a feeding lumen and an aspirating lumen. The aspirating lumen includes a set of primary aspirating orifices and a set of secondary aspirating orifices, and the feeding lumen includes an orifice positioned adjacent a distal end of the tube. The primary aspirating orifices function as main aspirating sites, while the secondary aspirating orifices act as suction breakers for the primary aspirating orifices. At predetermined points along the tube, there are placed a pair of aspirating orifices, each pair including a primary aspirating orifice and a secondary aspirating orifice.

When the gastrointestinal aspirating and feeding device disclosed in Moss '092 is surgically inserted within a patient's body, the feeding orifice is positioned in the proximal duodenum. Further, at least one pair of primary and secondary aspirating orifices are positioned within the terminal portion of the stomach, the pylorus and/or the proximal duodenum, and at least one pair of primary and secondary aspirating orifices are located within the main body of the stomach.

The gastrointestinal aspirating and feeding devices illustrated in Moss '089 and Moss '092 effectively remove swallowed air from the digestive system during surgery, and provide the digestive system with liquid nourishment immediately after surgery, without overfeeding. Advantageously, overfeeding in an average size patient is prevented by separating the feeding orifice a fixed distance of approximately three inches from the closest aspirating orifice. Such a separation allows the digestive system of an average size patient to absorb the maximum amount of nourishment it can handle, while aspirating any amount of overfeeding before the functioning of the digestive system is compromised. Specifically, peristaltic activity along about 3 inches (7–8 cm) of intestine prevents spontaneous retrograde flow, acting in effect as a "one-way valve". When feeding rates are not excessive to the patient's gastrointestinal function, the three inch separation between the feeding orifice and the closest aspirating orifice prevents inadvertent loss of nourishment. However, should the patient be overfed, only the excess will flow retrograde with a virtually unmeasurable pressure increase within the system and be withdrawn through the aspirating orifice.

Unfortunately, although the gastrointestinal aspirating and feeding devices disclosed in Moss '089 and Moss '092 may be adequately employed for any size patient, the devices do not allow the surgeon to precisely control the distal extent of aspiration according to the size of the patient, especially for those patients having very small stomachs because of age or gastric resection. Further, the fixed three inch distance between the feeding orifice and the closest aspirating orifice may prevent the surgeon from optimally controlling the removal of excess liquid nutrients from those patients having above-average or below-average sizes, potentially resulting in an undesirable overfeeding or underfeeding condition.

SUMMARY OF THE INVENTION

In order to avoid the disadvantages of the prior art, the present invention provides a gastrointestinal aspirating and feeding device having a removable sleeve for selectively obstructing a plurality of aspirating orifices. By selectively cutting-away a section of the removable sleeve, the distance between the distal feeding orifice and the closest operational aspirating orifice, as well as the distal extent of aspiration for any size patient, is optimized.

In accordance with a preferred embodiment of the present invention, the gastrointestinal aspirating and feeding device comprises a tube having a feeding lumen and an aspirating lumen. The feeding lumen includes an orifice positioned adjacent a distal end of the tube. The aspirating lumen includes a set of primary aspirating orifices, and a set of secondary aspirating orifices which act as suction breakers for the primary aspirating orifices. Along the tube, there are disposed several pairs of aspirating orifices, each pair including a primary aspirating orifice and a secondary aspirating orifice.

The pairs of aspirating orifices are divided into first and second groups along the length of the aspirating lumen, wherein the second group of pairs of aspirating orifices is located closest to the feeding orifice. The second group of pairs of aspirating orifices is covered with a removable, length adjustable sleeve, preferably formed from a section of a thin walled, elastomeric, silicone rubber tubing. Alternately, the sleeve may be formed of any suitable fluid and gas impermeable, bio-compatible material. Prior to surgical insertion, and depending upon the size and/or medical history of the patient, a surgeon may selectively remove part or all of the sleeve covering one or more pairs of the aspirating orifices in the second group, thereby exposing some or all of the underlying pairs of aspirating orifices.

When the gastrointestinal aspirating and feeding device is surgically inserted within a patient's body, the feeding orifice is positioned in the proximal duodenum. Further, after insertion, the second group of aspirating orifices is positioned within the terminal portion of the stomach, the pylorus and/or the proximal duodenum, and the first group of aspirating orifices is located within the main body of the stomach.

BRIEF DESCRIPTION OF THE DRAWINGS

These and other features of the present invention will become readily apparent upon reading the following detailed description and upon reference to the drawings in which:

FIG. 1 is an elevational view of a gastrointestinal aspirating and feeding device in accordance with a preferred embodiment of the present invention;

FIG. 2 is a cross-sectional view of the gastrointestinal aspirating and feeding device taken along line 2—2 in FIG. 1;

FIG. 3 is a cross-sectional view of the gastrointestinal aspirating and feeding device taken along line 3—3 in FIG. 1;

DETAILED DESCRIPTION OF THE INVENTION

Figure 4:
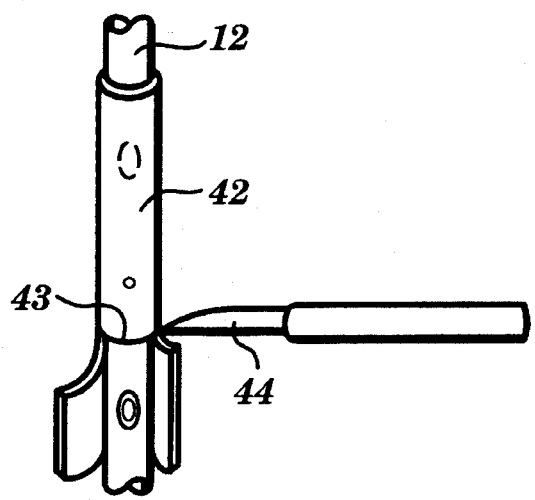
FIG. 4 illustrates the removal of the portion of the sleeve covering the pair of aspirating orifices closest to the feeding orifice, thereby exposing the underlying pair of aspirating orifices.

Referring now specifically to the drawings, there is illustrated a gastrointestinal aspirating and feeding device, generally designated as 10, in accordance with a preferred embodiment of the present invention, wherein like reference numerals refer to like components throughout the drawings.

As illustrated in FIG. 1, the gastrointestinal aspirating and feeding device 10, hereinafter referred to as a gastrointestinal device, generally comprises an elongated tube 12 incorporating an aspirating lumen 14, a feeding lumen 16 and an inflation lumen 18, each communicating with the outside of the tube 12 through at least one orifice. Toward a first end of the tube 12, the feeding lumen 16 and inflation lumen 18, which extend longitudinally through the outer periphery of the tube 12, separate from the tube, thus forming three individual, accessible lumens.

The tube 12, shown in cross-section in FIG. 2, incorporates the aspirating lumen 14, feeding lumen 16 and inflation lumen 18. Specifically, the aspirating lumen 14 is centrally located and forms the main bore of the tube 12. The feeding lumen 16 and inflation lumen 18 are disposed 180° apart from one another on either side of the aspirating lumen 14.

A first end of the feeding lumen 16 includes a feeding attachment 24 for receiving liquid nutrients therein. After entering the tube wall and extending longitudinally toward the distal end of the aspirating lumen 14, the second, opposing end of the feeding lumen 16 terminates at a feeding orifice 26. The feeding attachment 24 is designed to receive a male Luer fitting. A sealing cap 28, connected to the feeding attachment 24, is utilized to close the external end of the feeding lumen 16 when not in use.

A first end of the inflation lumen 18 includes an inflation attachment 30 for receiving a water-filled syringe (not shown). A second, opposing end of the inflation lumen 18 terminates at an inflation orifice 32 which communicates with the inside of a balloon 34. Accordingly, as known in the art, the balloon 34 can be inserted into a patient's body in a deflated state and subsequently inflated 34' (shown in phantom) with 10–30 ml. of sterile water.

An aspirating attachment 36, provided at a first end of the aspirating lumen 14, is designed to be connected to a source of suction. Two distinct groups of pairs of aspirating orifices, wherein each pair of aspirating orifices include a larger primary orifice 20 and a smaller secondary orifice 22, extend along the midportion of the aspirating lumen 14. The function of the pairs of aspirating orifices is fully disclosed in Moss '092 and will not be described further. A first group 38 of pairs of aspirating orifices is positioned adjacent the inflatable balloon 34. The second group 40 of pairs of aspirating orifices is positioned closer to the feeding orifice 26 found proximate the distal end of the tube 12. In accordance with a preferred embodiment of the present invention, the second group 40 of pairs of aspirating orifices is covered with a partially or wholly removable, length adjustable sleeve 42, preferably formed from a section of a thin walled, elastomeric, silicone rubber tubing having an inner diameter that is smaller than the outer diameter of the tube 12. Accordingly, the elastic nature of the sleeve 42 tightly secures the sleeve about the tube 12 over the second group 40 of pairs of aspirating orifices. The sleeve 42, as well as the underlying second group 40 of pairs of aspirating orifices, extend approximately two-five inches from the feeding orifice 26.

As shown in cross-section in FIG. 3, the sleeve 42 encircles the tube 12, obstructing the underlying primary and secondary orifices 20, 22. Again, the aspirating lumen 14 is centrally located and forms the main bore of the tube 12, while the feeding lumen 16 extends longitudinally through the wall of the tube 12.

The second group 40 of pairs of aspirating orifices is covered by suitably increasing the diameter of the sleeve 42 (e.g. by stretching) and inserting the tube 12 longitudinally therethrough until the second group 40 is positioned underneath the sleeve 42. After the tube 12 has been appropriately positioned, the sleeve 42 is released, thereby covering the second group 40 and obstructing the underlying pairs of aspirating orifices, rendering the orifices nonfunctional. As illustrated in FIG. 4, a surgeon may selectively cut away part, some, or all of the sleeve 42 using a scalpel 44, scissors or the like, thereby exposing and rendering operational some of all of, or the underlying pairs of aspirating orifices. Alternately, the sleeve 42 may include encircling perforations (not shown) located between each pair of primary and secondary aspirating orifices 20, 22. In this case, the surgeon may tear-away part or all of the sleeve 42 along the perforations to expose some or all of the obstructed aspirating orifices.

Figure 5:
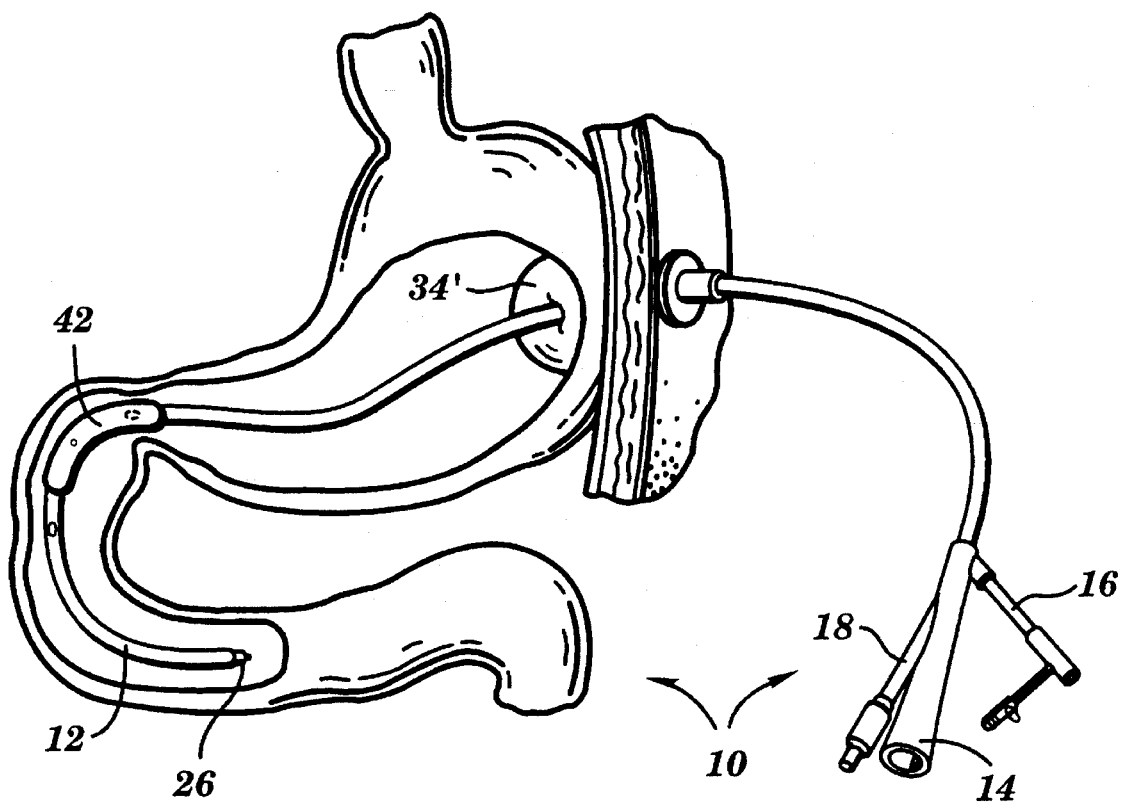
FIG. 5 shows the gastrointestinal aspirating and feeding device of the present invention disposed within the gastrointestinal tract of a patient, with the pair of aspirating orifices closest to the feeding orifice exposed as shown in FIG. 4.

Referring now specifically to FIG. 5, the distal end of the gastrointestinal tube 10 is inserted and positioned within the gastrointestinal tract of the patient after the desired pairs of aspirating orifices in the second group 40 have been exposed. The procedures for inserting and operating the gastrointestinal tube 10 are well known in the art and will not be described further. Upon proper insertion, the exposed pairs of aspirating orifices in the second group 40 may lie within the terminal portion of the stomach, the pylorus, and/or the proximal duodenum. In addition, the exposed pairs of aspirating orifices may lie within the jejunum if the patient has had a gastrojejunostomy.

As further illustrated in FIG. 5, the surgeon may easily control the distal extent of aspiration for any size patient by exposing some or all of the pairs of aspirating orifices in the second group 40. Further, the surgeon may carefully control the distance between the feeding orifice 26, disposed proximate the distal end of the gastrointestinal tube 10, and the nearest operational aspiration site to optimally regulate the removal (via aspiration) of "excess" feeding.

The foregoing description of the preferred embodiments of the invention has been presented for purposes of illustration and description. It is not intended to be exhaustive or to limit the invention to the precise form disclosed, and obviously many modifications and variations are possible in light of the above teaching. For example, the first and second groups of pairs of aspirating orifices may both be covered with a single removable, length adjustable sleeve, or individual, removable, length adjustable sleeves, wherein a surgeon may selectively remove portions of the sleeve(s) covering one or more pairs of the aspirating orifices in the first and second group, depending upon the operational requirements of a patient. Such modifications and variations that may be apparent to a person skilled in the art are intended to be included within the scope of this invention as defined by the accompanying claims.

I claim:

1. A gastrointestinal aspirating device comprising:

an elongated tube including an aspirating lumen defined by a wall, said wall having a plurality of aspirating orifices located therethrough; and a selectively removable elastic sleeve, located about a portion of the elongated tube and covering some of said plurality of aspirating orifices, for enabling an operator to remove a section of the selectively removable elastic sleeve from the tube to expose at least one of the aspirating orifices, wherein said elongated tube further includes a feeding lumen, said feeding lumen having an external end portion adapted to be positioned outside a patient's body for receiving a supply of food, said feeding lumen further having an internal end portion adapted to be positioned in a gastrointestinal section of said patient's body, said internal end portion having a feeding orifice for discharging said food, and wherein said elongated tube includes first and second distinct groups of aspirating orifices, said second group of aspirating orifices disposed closest to the feeding orifice, and wherein said selectively removable elastic sleeve covers the aspirating orifices in said second group.

2. A gastrointestinal aspirating device comprising:

an elongated tube including an aspirating lumen defined by a wall, said wall having a plurality of aspirating orifices located therethrough; and a cuttable elastic sleeve, located about a circumference of the elongated tube, for achieving both a first position that covers some of said plurality of aspirating orifices, and a second position achieved by removing a section of the sleeve from the elongated tube so that at least one of the covered aspirating orifices is exposed, wherein the elongated tub has an outside, and wherein said sleeve has an inside diameter diameter that is smaller than the outside diameter of the elongated tube, the inside diameter is sufficient to substantially inhibit relative movement between the sleeve and the elongated tube, and wherein said elongated tube further defines a feeding lumen located within a length of the wall of the elongated tube and being parallel to the aspirating lumen, said feeding lumen having an external end portion adapted to be positioned outside a patient's body for receiving a supply of food, said feeding lumen further having an internal end portion adapted to be positioned in a gastrointestinal section of said patient's body, said internal end portion having a feeding orifice for discharging said food.

3. The gastrointestinal aspirating device of claim 2, wherein said elongated tube includes first and second distinct groups of aspirating orifices, said second group of aspirating orifices disposed closet to the feeding orifice, and wherein said removeable sleeve covers the aspirating orifices in said second group.

4. A gastrointestinal aspirating device comprising:

a) an elongated tube including an aspirating lumen defined by a wall, said wall having a plurality of aspirating orifices located therethrough;

b) a selectively removable elastic sleeve, located about a portion of the elongated tube and covering some of said plurality of aspirating orifices, for enabling an operator to remove a section of the selectively removeable elastic sleeve from the tube to expose at least one of the aspirating orifices;

c) the elongated tube further comprises a feeding lumen located within the wall of the elongated tube and being parallel to the aspirating lumen, said feeding lumen having an external end portion adapted to be positioned outside a patient's body for receiving a supply of food, said feeding lumen further having an internal end portion adapted to be positioned in a gastrointestinal section of said patient's body, said internal end portion having a feeding orifice for discharging said food; and d) said elongated tube includes first and second distinct groups of aspirating orifices, said second group of aspirating orifices disposed closest to the feeding orifice, and wherein said selectively removable elastic sleeve covers the aspirating orifices in said second group.

* * * * *